United States Patent [19]

Tersteeg et al.

[11] 4,219,529
[45] Aug. 26, 1980

[54] INCUBATOR FOR CHEMICAL ANALYZER

[75] Inventors: Glenn E. Tersteeg, Honeoye Falls; Louis C. Nosco, Rochester; Robert J. Meyer, Spencerport; Rodney J. Whitcomb, Rochester, all of N.Y.

[73] Assignee: Eastman Kodak Company, Rochester, N.Y.

[21] Appl. No.: 855,124

[22] Filed: Nov. 28, 1977

Related U.S. Application Data

[63] Continuation of Ser. No. 751,911, Dec. 17, 1976, abandoned.

[51] Int. Cl.² ............................ G01N 33/16; G01N 1/14
[52] U.S. Cl. ................................................ 422/65; 422/64; 435/809
[58] Field of Search ................. 23/230 R; 422/64-66; 195/127, 139; 119/35, 39, 43; 435/809

[56] References Cited

U.S. PATENT DOCUMENTS

| | | | |
|---|---|---|---|
| 2,055,021 | 9/1936 | Wall | 74/426 |
| 2,560,107 | 7/1951 | Hewson | 23/253 |
| 2,797,149 | 6/1957 | Skeggs | 422/82 |
| 3,036,893 | 5/1962 | Natelson | 23/230 |
| 3,526,480 | 9/1970 | Findl et al. | 23/253 R |
| 3,556,731 | 1/1971 | Martin | 23/253 R |
| 3,562,114 | 2/1971 | Steidl et al. | 195/139 |
| 3,574,064 | 4/1971 | Binnings et al. | 195/127 |
| 3,616,264 | 10/1971 | Ray | 195/127 |
| 3,618,734 | 11/1971 | Khan | 195/127 |
| 3,728,227 | 4/1973 | Elson et al. | 195/127 |
| 3,756,920 | 9/1973 | Kelbaugh et al. | 195/127 |
| 3,758,274 | 9/1973 | Ritchie et al. | 23/259 |
| 3,770,382 | 11/1973 | Carter et al. | 422/61 |
| 3,788,816 | 1/1974 | Rohrbaugh et al. | 23/253 R |
| 3,853,711 | 12/1974 | Heden | 195/127 |
| 3,904,369 | 9/1975 | Adler et al. | 23/230 R |

FOREIGN PATENT DOCUMENTS

1210904 11/1970 United Kingdom.

*Primary Examiner*—R. E. Serwin
*Attorney, Agent, or Firm*—D. D. Schaper

[57] ABSTRACT

An incubator is provided for use with a chemical analyzer of the type in which a fluid sample is metered onto a test slide which is analyzed after a suitable period of incubation. The incubator includes a temperature-controlled chamber having a conveyor mounted therein which comprises a plurality of slide holding members. A drive means for the conveyor is adapted to successively advance the slide holding members past load and unload slots located adjacent slide transfer mechanisms.

14 Claims, 5 Drawing Figures

INCUBATOR FOR CHEMICAL ANALYZER

CROSS-REFERENCE TO RELATED APPLICATIONS

This application is a continuation of copending application Ser. No. 751,911, filed Dec. 17, 1976, now abandoned.

Reference is made to commonly-assigned U.S. patent applications: Ser. No. 751,872, entitled METHOD AND APPARATUS FOR CHEMICAL ANALYSIS, filed in the name of Clyde P. Glover et al., on Dec. 17, 1976; U.S. application Ser. No. 751,873, entitled INCUBATOR AND RADIOMETRIC SCANNER, filed in the name of Edward Muka et al., on Dec. 17, 1976, and now U.S. Pat. No. 4,119,381; and U.S. application Ser. No. 751,912, entitled CHEMICAL ANALYZER, filed in the name of L. Nosco et al., on Dec. 17, 1976, and now U.S. Pat. No. 4,152,390.

BACKGROUND OF THE INVENTION

1. Field of the Invention

This invention relates to chemical apparatus for the automatic analysis of biological fluids, and more particularly, to an incubator for use in such apparatus.

2. State of the Prior Art

In recent years, a number of automated systems have been developed for carrying out quantitative chemical analyses of fluid samples. Most of the commercially-available systems utilize liquid reagents and require analyzer equipment having intricate solution handling and transport capabilities. One widely used system, shown in U.S. Pat. No. 2,797,149, employs a continuous-flow technique in which successive samples are separated from one another by immiscible fluid segments such as gas or air bubbles. Such a system is complex and expensive, requires skilled operators, and necessitates cleaning operations.

In clinical analyzers for measuring a characteristic of a substrate in liquid form, incubators are employed to bring the substrate to a desired state for analysis. These incubators generally comprise: a plurality of stations for the substrates, often mounted for rotation about an axis; a temperature control system including a heater; and a radiometer of some type, such as a reflectometer, designed to selectively scan each of the stations. A relatively simple example of such an incubator is shown in U.S. Pat. No. 3,616,264, whereas U.S. Pat. Nos. 3,756,920; 3,758,274; 3,788,816 and 3,790,346 illustrate more complex apparatus. In this art, however, no provision is made for an incubator in which substrates can be readily moved in and out of a conveyor contained within the incubator.

As an alternative to liquid analysis systems, various essentially-dry analytical elements have been adopted for automated test procedures. Although these elements offer substantial storage, handling and other conveniences, as compared to "wet-chemistry," they have enjoyed only limited success and have been used primarily for qualitative and semiquantitative test purposes. Apparatus for use with analytical elements in the form of continuous webs is shown in U.S. Pat. Nos. 3,036,893, and 3,526,480. In this apparatus, the web is passed through a relatively simple incubation station; however, since the reagents are contained on the web in a predetermined sequence, the versatility of this apparatus is quite limited.

The Binnings et al., U.S. Pat. No. 3,574,064, discloses apparatus in which glass slides are fed from a single supply station onto a turntable. Slides carried on the turntable are moved past a metering station, and then through wash and incubation stations spaced around the periphery of the turntable. Slides processed by the apparatus are ejected from the turntable into a slide receiver adjacent the slide supply station. There is no provision for automatic analysis of the processed slides, and they must be manually removed from the slide receiver for examination under a laboratory microscope.

U.S. Pat. No. 3,770,382, to Carter et al. discloses a clinical analyzer in which test packs containing a sample fluid and reagents are carried on a continuous chain which moves the packs through a plurality of stations in a heat-controlled chamber. Mounted within the chamber, at the entrance thereof, is a preheater which is adapted to raise the test packs to a desired temperature range. Since the Carter et al. heat-controlled chamber is large enough to include most of the analyzer components, including the analysis means, considerable heating equipment is required to maintain a precise temperature control.

The Wall, U.S. Pat. No. 2,055,021, discloses an intermittent drive mechanism comprising a worm in which a first thread portion has a zero helix angle and a second thread portion is disposed at an angle to the first thread portion. There is no suggestion in this patent of the use of such a drive mechanism in a chemical analyzer.

OBJECTS OF THE INVENTION

It is the object of the invention to provide an improved incubator, for use with a chemical analyzer of the type which employs test slides, in which slides can be readily transferred between the incubator and elements of the analyzer by means of a slide conveyor which cooperates with a plurality of transfer mechanisms.

It is a related object of the invention to provide, in apparatus of the type described, a means for preheating test slides prior to loading the slides in an incubator.

It is a further object of the invention to provide an incubator for a chemical analyzer in which drive means are adapted to stop slide holding members in a precise location relative to slide loading and unloading means.

Other objects and advantages will become apparent by reference to the following Summary and Description of Preferred Embodiments, together with the attached drawings.

SUMMARY OF THE INVENTION

This invention relates to an incubator for use with apparatus for the automatic analysis of biological fluids in which a fluid sample is metered onto a test slide which is analyzed after a suitable period of incubation.

In accordance with the invention, there is provided an incubator for use in a chemical analyzer in which a fluid sample is metered onto a slide which is analyzed after an appropriate period of incubation, said incubator comprising: means which defines a temperature controlled chamber, said chamber having a first location wherein slides are transferred into the chamber and a second location wherein slides are transferred out of the chamber; conveyor means in said chamber, said conveyor means including a plurality of slide holding means for releasably holding the slides in the conveyor means; and drive means for said conveyor means, said drive means being adapted to effect movement of slides in the conveyor means within said chamber, and said drive means being further adapted to stop said conveyor means in a position such that slides can be transferred at either of said locations.

The invention is particularly suitable for use in apparatus adapted to perform analyses of blood sera in which the serum is dispensed onto a test element, or test slide, of the type which is formed as a multilayer element containing the necessary reagents for reaction with components of the serum. However, this invention is not limited to use with just such test slides, nor is it limited to just the analysis of blood sera, as other fluids can be used with apparatus of the type disclosed.

DESCRIPTION OF THE PREFERRED EMBODIMENT

Figure 1:
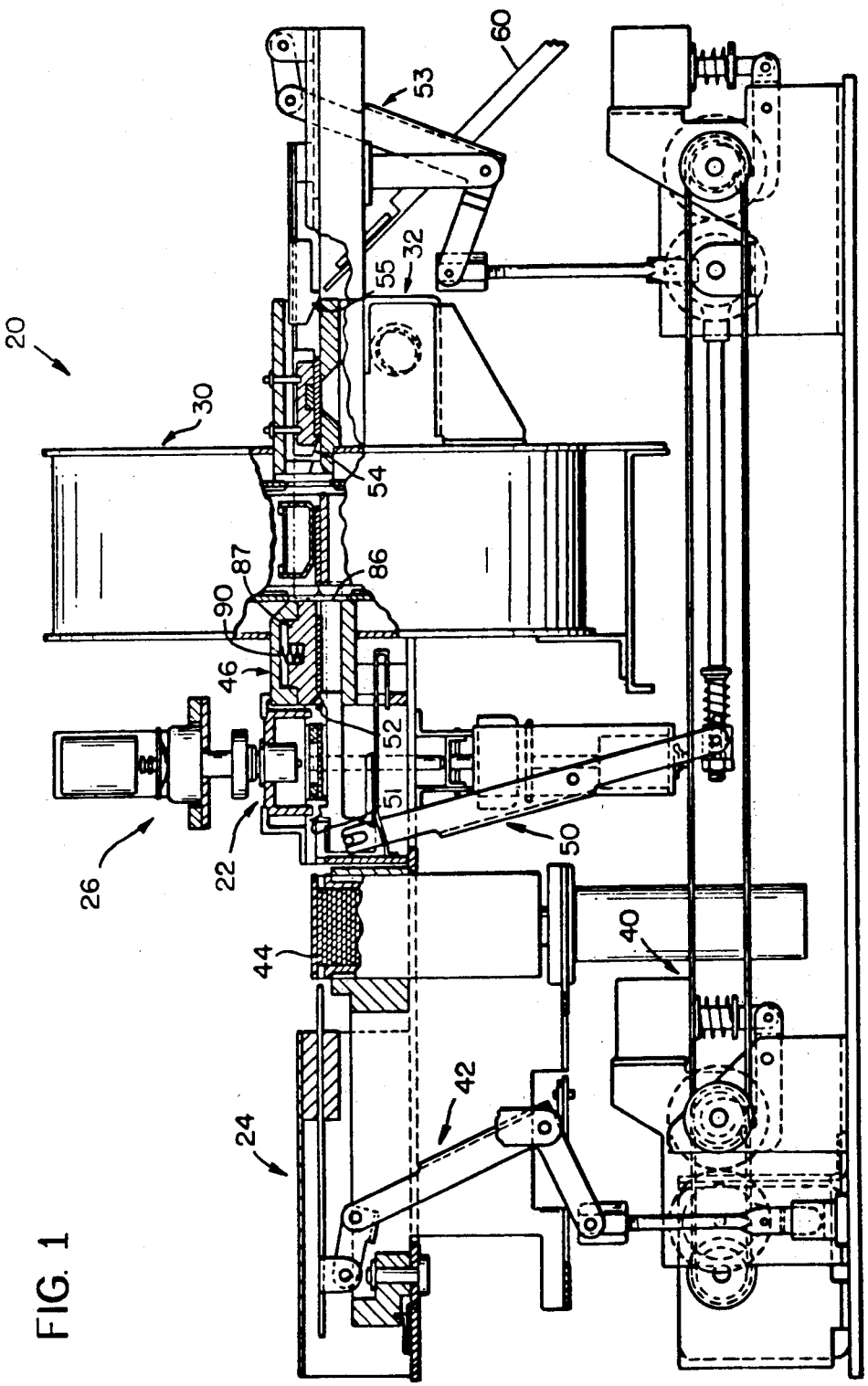
FIG. 1 is an elevational view, partially in section, of a chemical analyzer of the type which employs the incubator of the subject invention.

The incubator of the subject invention is particularly suitable for use with a chemical analyzer of the type shown in FIG. 1 which is described and claimed in the aforesaid U.S. application Ser. No. 751,912, entitled CHEMICAL ANALYZER. With reference to FIG. 1, there is shown a chemical analyzer 20 which comprises a sample tray 22, a reagent supply table 24, a metering device 26, an incubator 30, and analysis means 32. A slide handling mechanism 40 comprises an ejector mechanism 42 which is adapted to move a test element, such as a test slide 44, into a metering station where a drop of biological fluid is placed thereon, a forward transfer mechanism 50 which has a first claw mechanism 51 adapted to move a slide 44 from the metering station to a preheater 46 and a second claw mechanism 52 for moving a slide from the preheater to incubator 30, and a rear transfer mechanism 53 having claw mechanisms 54 and 55 for moving a slide from the incubator 30 to analysis means 32 and from analysis means 32 into a disposal chute 60.

A highly preferred form of slide for use with the disclosed apparatus is shown in Belgian Pat. No. 801,402, granted on Jan. 2, 1974. The slides disclosed in the Belgian patent are formed as a multilayer element containing the necessary reagents for reaction with components of a biological fluid, such as blood serum, deposited thereon. Certain reactions colorimetrically produce a change in optical density which is sensed by a reflectometer, the amount of light reflected from the element varying in accordance with the reaction and being indicative of the amount of a particular component present in the fluid.

Figure 2:
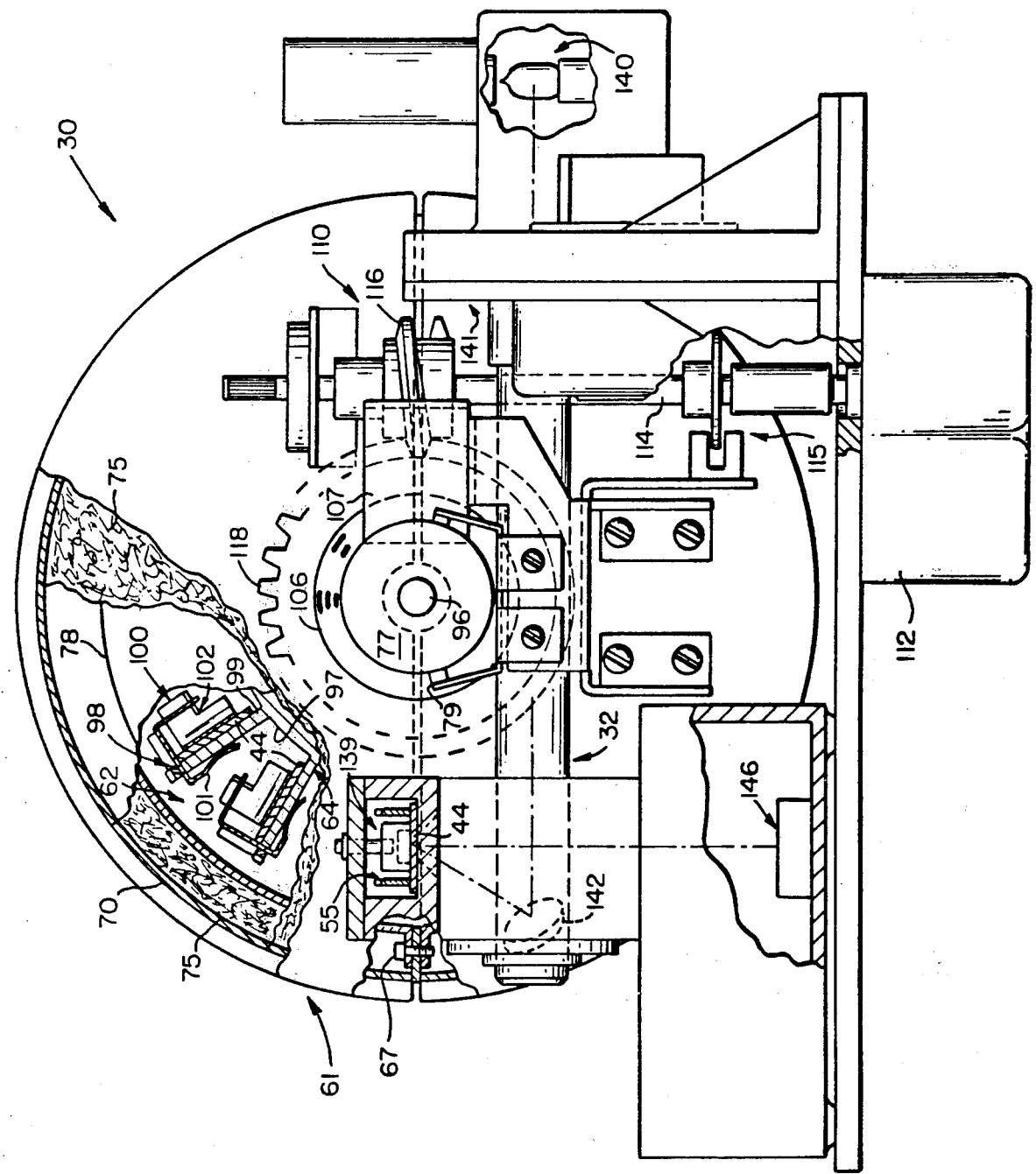
FIG. 2 is an elevational view of the incubator constructed in accordance with the invention, with portions broken away to show the incubator rotor and the reflectometer.
Figure 3:
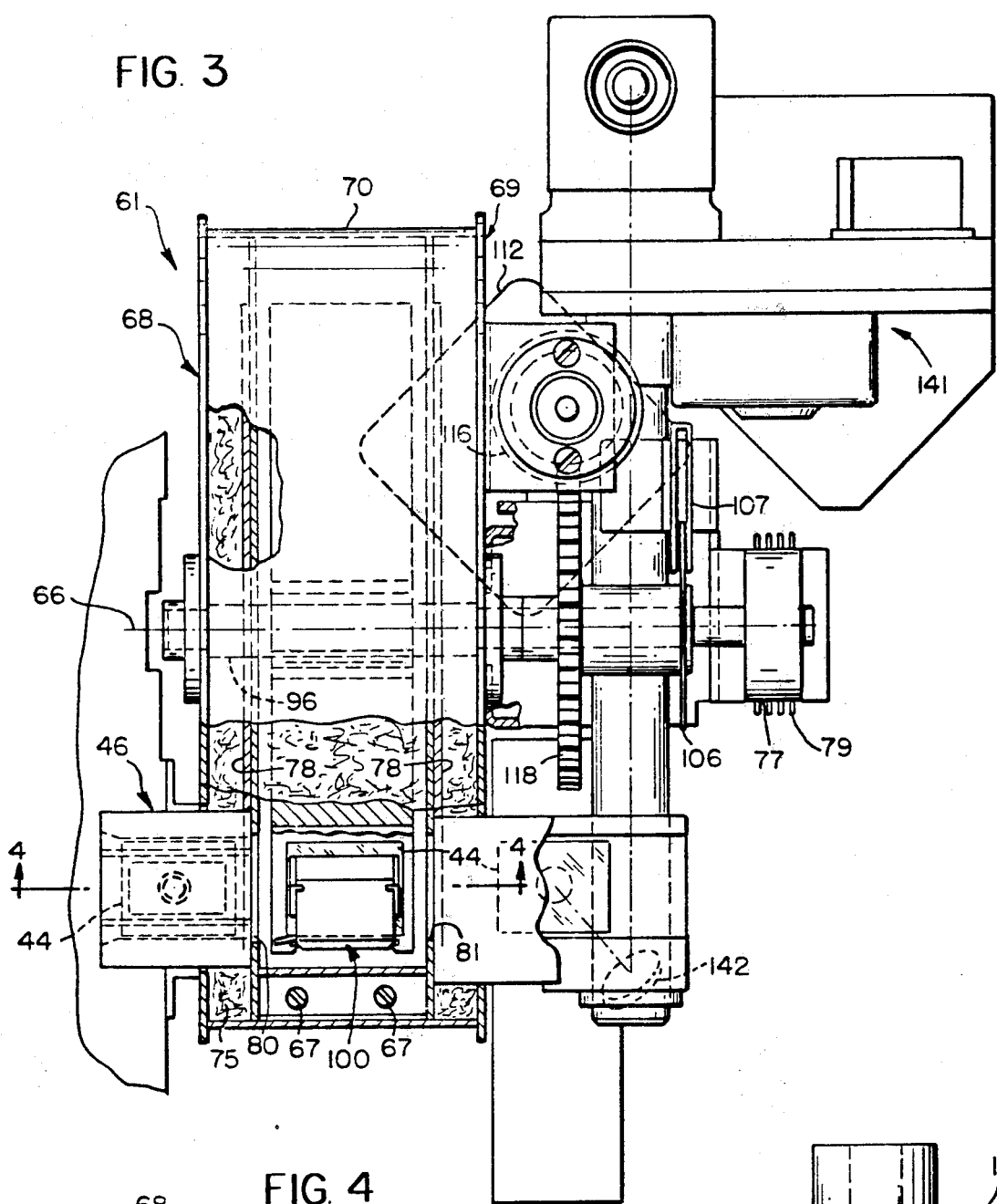
FIG. 3 is a top plan view of the incubator shown in FIG. 2.

In FIGS. 2 and 3, there is shown an incubator 30 which comprises a housing 61 which defines a generally cylindrical, temperature-controlled chamber 62, a rotor 64 mounted for rotation within chamber 62 about a horizontal axis designated 66, preheater 46, and a drive mechanism 110 for rotor 64.

The housing 61 is formed in sections joined by fasteners 67 and comprises a pair of end walls 68, 69, joined by a cylindrical wall 70. Each of the walls includes a double thickness of a suitable metal separated by a layer of insulation 75. Heating elements 78, which may be of the type in which high resistance wires are embedded in silicone rubber, are affixed to walls 68, 69, as shown in FIG. 3. Heating elements 78 are connected to a control circuit, not shown, which includes thermistors in a feedback arrangement to control power to elements 78 for maintaining chamber 62 at a constant temperature, preferably 37° C. One of the thermistors is located in rotor 64, and is connected to the control circuit through slip rings 77 and brushes 79. A load slot 80 is provided in wall 68, and an unload slot 81 is provided in wall 69. (See FIG. 3.) Slots 80, 81, are of a shape and size sufficient to allow the free passage of a slide 44 and the appropriate transfer mechanism, as described hereinafter.

Figure 4:
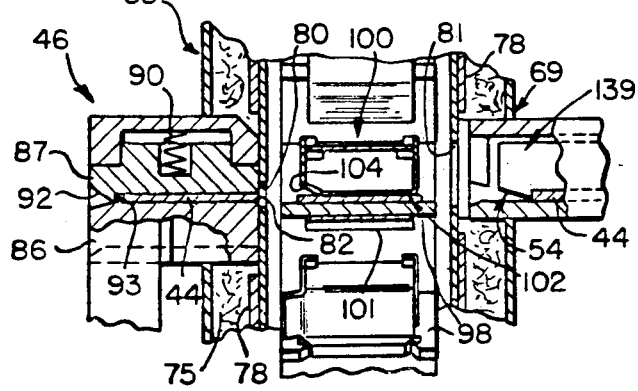
FIG. 4 is a sectional view, taken along the line 4—4 in FIG. 3.

With reference to FIG. 4, preheater 46 is supported relative to housing 61 such that an exit opening 82 communicates with load slot 80 of incubator 30. Preheater 46 comprises an electrically-heated metal block 86 and a pressure pad 87 which is biased toward block 86 by spring 90. When a slide 44 is moved into preheater 46 by claw mechanism 51, the contact of slide 44 with beveled edge 92 on pressure pad 87 will cam the pad upwardly against spring 90 to permit the slide to be moved into the preheater. An anti-backup tab 93 on pad 87 prevents the slide in the preheater from moving back out of preheater 46, as claw mechanism 52 returns to its forward position. Preheater 46 is adapted to raise a slide 44 from ambient temperature to a temperature near the temperature maintained in the incubator chamber 62. Thus, a slide entering chamber 62 does not materially affect the temperature therein, and a very precise temperature control can be maintained in the chamber.

Mounted for rotation within chamber 62 of housing 61 is rotor 64 which serves as a circular slide conveyor for moving slides in a rotary path about axis 66; axis 66 is generally parallel to the direction of slide movement into and out of chamber 62. As best shown in FIGS. 3 and 4, slides are loaded into, and unloaded from, housing 61 in a substantially straight-line movement. Rotor 64 comprises a rotor shaft 96 journaled in housing 61, and a hub 97 fixedly mounted to shaft 96. A plurality of slide holding means are carried on hub 97, the slide holding means comprising radially extending support members 98. (See FIG. 2.) Spring clips 100 are mounted on members 98 and are adapted to releasably hold a slide 44 against a surface 99 on each member 98. Clip 100 comprises a generally U-shaped flexible element 101 which is fixed to member 98 and supports a pressure member 102. It will be apparent that clip 100 could also be formed as an integral unit.

Each of the claw mechanisms 52, 54, which are operable to transfer slides between rotor 64 and the analyzer elements, comprises spaced members which pass on opposite sides of pressure member 102 as the claw mechanisms move in and out of the chamber 62. As shown in FIG. 4, a forward edge portion 104 of the member 102 is shaped such that a slide 44 contacting the edge, as it moves into the incubator, will cause element 101 to be flexed sufficiently to permit the slide to move between pressure member 102 and surface 99. An encoder wheel 106, carried on shaft 96, cooperates with a detector 107 to provide a means for locating a particular member 98 on rotor 64.

Figure 5:
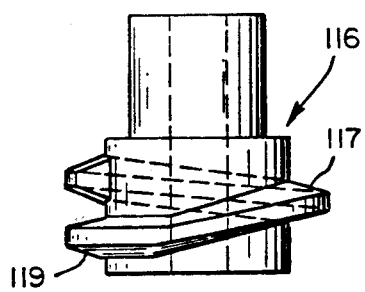
FIG. 5 is an enlarged elevational view of the worm for the incubator drive mechanism.

With reference to FIGS. 2 and 3, there is shown a drive mechanism 110 which is provided to advance rotor 64 in precise increments and to hold the rotor in position during loading and unloading operations. Drive mechanism 110 comprises a motor 112 which is operatively connected to a shaft 114 which carries a worm 116 thereon. Worm 116 is adapted to cooperate with a worm wheel 118 mounted on rotor shaft 96. Worm 116 and worm wheel 118 are designed such that one revolution of shaft 114 will advance rotor 64 sufficiently to move one slide handling member out of the load position and the next slide handling member into the load position. As shown in FIG. 5, worm 116 has a thread 117 having a portion 119 disposed at a zero helix angle, i.e., there is no lead in this thread portion. This arrangement facilitates the precise positioning of a slide holding means relative to the load and unload slots and to the slide transfer mechanisms, since the rotor is always stopped with the portion 119 in contact with wheel 118. A sensing mechanism 115 is adapted to cut power to motor 112 after one complete revolution of shaft 114, and just as thread portion 119 enters into driving engagement with wheel 118. Thus, if motor shaft 114 continues to turn for an instant after power is cut to motor 112, rotor 64 will not be moved out of position, since no movement of rotor 64 occurs when thread portion 119 is in engagement with wheel 118. It will also be apparent that by selecting the proper speed for motor 112, length of thread portion 119, and sequence of operation of transfer mechanisms 50, 53, it would be possible to continuously drive motor 112 during the loading and unloading operations.

Slides are moved out of the incubator 30 through unload slot 81 and are moved into a chamber 139 in analysis means 32. Analysis means 32, which is supported in incubator wall 69, is adapted to obtain a reflectance reading of a slide 44. As shown in FIG. 2, analysis means 32 comprises a light source 140, here shown as an incandescent bulb, a filter system shown at 141, a lens system, not shown, a mirror 142 which directs a beam of light against a slide 44 in the chamber 139, and a detection means shown at 146.

In operation, slides 44 are sequentially loaded into incubator 30 after a predetermined time in preheater 46. Analyzer 20 is adapted to be continuously operated and the temperature within incubator 30 is controlled such that slides are ready to be analyzed after they have made one revolution in incubator 30.

A control system for incubator 30, as well as for other functions of analyzer 20, could include a computer, not shown, which may take any of the various forms known in the art that include programmable minicomputers and programmable microprocessors. The instructions and method of programming such computers is well known in the art, and thus, no further explanation is considered necessary. In the use of such a computer, input data including sample identification, calibration values, and desired tests for each sample would be keyed into the computer. Output signals from the computer would be utilized to provide input signals to the analyzer components to control their operation at the appropriate time in the machine cycle. Results from analysis means 32 would be transmitted to the computer which would perform the necessary calculations, according to a stored program, to arrive at a concentration for a particular sample. This information, along with sample identification would then be transmitted to a display or printout device.

The invention has been described in detail with particular reference to certain preferred embodiments thereof, but it will be understood that variations and modifications can be effected within the spirit and scope of the invention.

What is claimed is:

1. An incubator for use in a chemical analyzer in which a fluid sample is metered onto a slide which is analyzed after an appropriate period of incubation, said incubator comprising:
   means which defines a temperature controlled chamber, said chamber having a first location wherein slides are transferred into the chamber and a second location wherein slides are transferred out of the chamber;
   rotor means in said chamber, said rotor means including a plurality of radially-extending slide holding means for releasably holding the slides in the rotor means; and
   drive means for said rotor means, said drive means being adapted to effect movement of slides in the rotor means within said chamber, and said drive means being further adapted to stop said rotor means in a position such that slides can be transferred at either of said locations.

2. An incubator, as defined in claim 1, wherein said means for defining a temperature controlled chamber comprises a first side wall mounted on one side of said rotor means and a second side wall mounted on an opposite side thereof, a load slot is in said first side wall at said first location, an unload slot is in said second wall at said second location, and said slots are in alignment with each other.

3. An incubator, as defined in claim 1, wherein said drive means comprises a worm which is coupled to said rotor means, and a thread portion of said worm is disposed at a zero helix angle.

4. An incubator, as defined in claim 2, wherein said rotor means moves the slides about an axis generally parallel to the direction of slide movement into and out of said chamber.

5. An incubator, as defined in claim 2, wherein analysis means is located adjacent said unload slot, and a slide transfer mechanism adjacent said unload slot is adapted to simultaneously move a first slide out of said rotor means and into said analysis means and a second slide out of said analysis means and into a discharge chute.

6. An incubator, as defined in claim 5, wherein each of said slide holding means comprises a support member and a spring clip mounted thereon, said clip having a portion which is adapted to be biased against a slide on the support member, said slide transfer mechanism comprises a claw mechanism having a pair of members, one of said members being located radially outward of said portion and the other member being located radially inward of said portion whereby said members are on opposite sides of the portion when the claw mechanism is in contact with the slide on said support member.

7. An incubator, as set forth in claim 6, wherein said preheater means comprises a heated portion of said means for loading slides into said carrier.

8. An incubator, as set forth in claim 6, wherein said preheater means comprises a heated surface which the slides contact during movement to the conveyor.

9. An incubator for use in a chemical analyzer of the type in which a fluid sample is metered onto a test slide which is analyzed after an appropriate period of incubation, said incubator comprising:

a housing which defines a temperature controlled chamber, said housing having a load slot on one wall thereof and an unload slot on an opposite wall, said slots being directly opposite each other;

a rotor mounted for rotation within said chamber, said rotor comprising a plurality of radially extending slide holding means; and drive means for said rotor, said drive means being adapted to successively move said slide holding means between said slots and to stop a selected one of said slide holding means in a position relative to said slots wherein a processed slide is unloaded from said one slide holding means through said unload slot and a new slide is loaded into said one slide holding means through said load slot.

10. An incubator as set forth in claim 9, wherein the rotor rotates about an axis which is generally parallel to the direction of movement of slides through said load and unload slots.

11. An incubator, as defined in claim 9, wherein a preheater is mounted adjacent said one wall and in communication with said load slot, said preheater comprising first and second elements which define a confined space slightly larger than a slide, said first element being adapted to be heated to a controlled temperature, and said second element being movable relative to said first element to permit entry of a slide into said preheater.

12. An incubator, as recited in claim 11, wherein said drive means comprises a rotor drive shaft, a ring gear mounted on said shaft, and a worm which cooperates with said ring gear, said worm including a thread having a zero helix angle in each 360 degree extension thereof.

13. An incubator, as recited in claim 12, wherein said slide holding means comprises a plurality of support members extending radially from a hub of said rotor, a spring clip is mounted on each of said members, each of said clips having a forward edge portion, and each of said clips being adapted to be cammed away from a surface on said member by the action of slide on said edge portion as the slide enters the rotor from said load slot.

14. An incubator for use in a chemical analyzer in which a fluid sample is metered onto a slide which is analyzed after an appropriate period of incubation, said incubator comprising:

a circular conveyor for moving slides through a rotary path;

means enclosing said conveyor to provide a controlled environment for slides during such movement;

means for loading slides bearing said fluid sample into said conveyor through a load slot in said enclosing means; and slide preheater means disposed adjacent said load slot for receiving slides and raising the temperature thereof prior to movement of the slides into said incubator.

* * * * *

UNITED STATES PATENT OFFICE
CERTIFICATE OF CORRECTION

PATENT NO. : 4,219,529

DATED : Aug. 26, 1980

INVENTOR(S) : Glenn E. Tersteeg, Louis C. Nosco, Robert J. Meyer, Rodney J. Whitcomb It is certified that error appears in the above-identified patent and that said Letters Patent are hereby corrected as shown below:

Column 6, Line 61   Please delete "6" and substitute therefor --14--

Column 6, Line 64   Please delete "6" and substitute therefor --14--

Signed and Sealed this

Tenth Day of August 1982

[SEAL]

Attest:

GERALD J. MOSSINGHOFF

Attesting Officer   Commissioner of Patents and Trademarks